United States Patent
Yao

(10) Patent No.: US 10,796,784 B2
(45) Date of Patent: Oct. 6, 2020

(54) MASS SPECTROMETRIC DATA ANALYZING APPARATUS AND ANALYZING METHOD

(71) Applicant: SHIMADZU CORPORATION, Kyoto-shi, Kyoto (JP)

(72) Inventor: Jingwen Yao, Sale (GB)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 1050 days.

(21) Appl. No.: 14/471,825

(22) Filed: Aug. 28, 2014

(65) Prior Publication Data

US 2015/0066380 A1 Mar. 5, 2015

(30) Foreign Application Priority Data

Aug. 30, 2013 (JP) .................................. 2013-178769

(51) Int. Cl.
*G01N 33/48* (2006.01)
*G16B 30/00* (2019.01)
*H01J 49/00* (2006.01)
*G16B 40/00* (2019.01)
*G06G 7/58* (2006.01)

(52) U.S. Cl.
CPC ............. *G16B 30/00* (2019.02); *G16B 40/00* (2019.02); *H01J 49/0036* (2013.01)

(58) Field of Classification Search
None
See application file for complete search history.

(56) References Cited

FOREIGN PATENT DOCUMENTS

| JP | 2011-215060 A | 10/2011 |
| JP | 2013-47624 A | 3/2013 |
| JP | 2013-88377 A | 5/2013 |

OTHER PUBLICATIONS

Maria Falth, et al., "Validation of Endogenous Peptide Identifications Using a Database of Tandem Mass Spectra", Journal of Proteome Research, 2008, pp. 3049-3053, vol. 7, No. 7.
M. Mann, et al., "Error-Tolerant Identification of Peptides in Sequence Databases by Peptide Sequence Tags", Analytical Chemistry, 1994, pp. 4390-4399, vol. 66, No. 24.
Gerben Menschaert, et al., "A Hybrid, de Novo Based, Genome-Wide Database Search Approach Applied to the Sea Urchin Neuropeptidome", Journal of Proteome Research, 2010, pp. 990-996, vol. 9, No. 2.
Gerben Menschaert, et al., "Spectral Clustering in Peptidomics Studies Allows Homology Searching and Modification Profiling: HomClus, a Versatile Tool", Journal of Proteome Research, 2012, pp. 2774-2785, vol. 11.
Communication dated Sep. 6, 2016 from the Japanese Patent Office in counterpart application No. 2013-178769.

*Primary Examiner* — Eric S Dejong
(74) *Attorney, Agent, or Firm* — Sughrue Mion, PLLC

(57) ABSTRACT

A tag database establishment section converts, based on information such as an amino acid sequence of an identified peptide and m/z of a peak, a sequence tag indicating a partial sequence and information related to the tag into a database and creates a tag database. When MS2 spectrum information is obtained by measuring a target peptide, a sequence tag acquisition section executes, on the tag database, a search based on coincidence of the m/z of the peak and the like and extracts a sequence tag with high reliability. A peptide identification section performs, based on an amino acid sequence of the sequence tag, m/z of a precursor ion, and the like, a search by a sequence tag search method taking into account a post-translational modification or a variation and identifies a peptide.

12 Claims, 8 Drawing Sheets

Fig. 4

| | Tag | MassIonB | MassIonY | PilotPeak1 | PilotPeak2 | ModificationInTag | ModLocation | ProteinID | PeptideID |
|---|---|---|---|---|---|---|---|---|---|
| 52 | EHF | (690.3443,1966.6);(819.3863,0)... | (147.1133,0);(294.1813,2665.2)... | 690.34 | 1103.51 | 0 | 0 | 1 | 5 |
| 53 | DPH | (116.0343,0);(231.0618,4844.1)... | (1090.4869,10034.2);(1227.545... | 465.17 | 1324.59 | 0 | 0 | 1 | 5 |
| 54 | PHA | (231.0618,4844.1);(328.1148,52... | (1019.4499,0);(1090.4869,1033... | 465.17 | 536.21 | 0 | 0 | 1 | 6 |
| 55 | HAC | (328.1149,5261.4);(465.1738,17... | (859.4193,10529.3);(1019.4499... | 465.17 | 696.24 | 1 | 3 | 1 | 6 |
| 56 | ACY | (465.1738,17478.9);(536.2108,1... | (859.3563,14288.8);(696.3563,14288... | 465.17 | 859.41 | 1 | 2 | 1 | 6 |
| 57 | CYS | (536.2108,13487.2);(696.2414,1... | (609.3243,0);(696.3563,14288... | 696.24 | 536.21 | 1 | 1 | 1 | 6 |
| 58 | YST | (696.2414,14288.8);(859.3044,1... | (508.2753,5976.4);(609.3243,0)... | 696.24 | 859.41 | 0 | 0 | 1 | 6 |
| 59 | NTL | (551.3198,0);(665.3628,0);(766... | (698.2809,4245.5);(811.3649,3... | 879.49 | 698.28 | 0 | 0 | 1 | 7 |
| 60 | TLC | (665.3628,0);(766.4108,2669.2)... | (538.2803,0);(698.2809,4245.5)... | 879.49 | 811.36 | 1 | 3 | 1 | 7 |
| 61 | LCD | (766.4108,2669.2);(879.4948,34... | (423.2223,0);(538.2503,0);(698... | 879.49 | 766.41 | 1 | 2 | 1 | 7 |
| 62 | PNT | (454.2662,0);(551.3198,0);(665... | (611.3649,3038.3);(912.4129,0)... | 766.41 | 1123.50 | 0 | 0 | 1 | 7 |
| 63 | VNE | (114.0918,0);(213.1598,4600.4)... | (708.3923,1746.2);(837.4343,1... | 456.24 | 213.15 | 0 | 0 | 1 | 9 |
| 64 | NEL | (213.1593,4600.4);(327.2028,39... | (595.3083,5553.8);(708.3923,1... | 456.24 | 595.30 | 0 | 0 | 1 | 9 |

MASS SPECTROMETRIC DATA ANALYZING APPARATUS AND ANALYZING METHOD

TECHNICAL FIELD

The present invention relates to a mass spectrometric data analyzing apparatus and analyzing method for processing and analyzing data collected by an $MS^n$ analysis (n is an integer equal to or larger than 2) on a test sample including a peptide and a protein to identify the peptide and the protein in the test sample.

BACKGROUND ART

In recent years, structural and functional analyses of proteins have been rapidly promoted as post-genome research. As one method for such structural and functional analyses of proteins (proteome analyses), an expression analysis or primary structure analysis of a protein using a mass spectrometer has been widely performed. A so-called $MS^n$ analysis, which includes the steps of capturing a specific kind of ion and dissociating the ion by collision induced dissociation (CID) or similar process within a quadrupole ion trap or the like, has proven itself to be a powerful technique.

A general process of identifying a protein by $MS^n$ analysis is as follows: A sample of the protein is broken into peptide fragments by a chemical process or enzymatic digestion. The obtained mixture of peptide fragments is subjected to mass spectrometry to obtain a mass spectrum ($MS^1$ spectrum). Subsequently, from the mass spectrum data of the mixture of the peptide fragments, a group of isotope peaks originating from a single peptide is selected as precursor ions. Then, these precursor ions are dissociated into fragment ions by collision induced dissociation, and a mass spectrometry of these fragment ions, i.e. the $MS^2$ analysis, is performed. By the collision induced dissociation process, the amino acid sequence making up a specific peptide has its bonds broken at various positions, and divided into fragments having different amino acid residues. Therefore, the obtained $MS^2$ spectrum reflects the amino acid sequence and structure of that specific peptide.

A most widely used method of directly identifying a peptide and a protein from such an $MS^2$ spectrum is an MS/MS ion search method. In the MS/MS ion search method, an imaginary CID spectrum is figured out by calculating fragmentation in a computer with respect to peptide obtained by digesting a protein stored in a protein database, using an enzyme actually used for sample composition. A peptide whose imaginary CID spectrum has high coincidence with an $MS^2$ spectrum obtained by actual measurement is searched for in the database. An expected value indicating reliability of the coincidence of the spectra is calculated taking the molecular weight information of the peptide (i.e., mass information of a precursor ion) into consideration. The peptide is identified based on the expected value. As a tool (computer software) for performing such an MS/MS ion search, "X!tandem" and "Mascot MS/MS ion search" provided by the British manufacturer Matrix Science Ltd. are well known.

In the MS/MS ion search method, it is possible to limit a search object space by adding constraint conditions in performing a database, by which a false positive can be reduced and the reliability of identification is improved. One of important constraint conditions in the database search is designation of a cutting part of a protein by enzymatic digestion.

However, the designation of the cutting part is not always possible for all peptides. For example, peptides such as a bioactive peptide (an endogenous peptide) produced by a precursor protein in a living organism are not cut by a specific digestive enzyme or the like. Therefore, when such peptides are identified by the MS/MS ion search method, a cutting part by an enzyme or the like cannot be designated. Therefore, with the previously described general peptide identifying method, it is difficult to identify the bioactive peptide and the like at high reliability. Further, in the bioactive peptide, a post-translational modification (PTM) and variations frequently occur. In the identifying method, the search object space expands when unknown post-translational modification or variation occurs. This makes it more difficult to correctly identify the peptide. On the other hand, as a method of identifying the bioactive peptide, methods explained below are known.

(1) SwePep Method (see Non Patent Literature 1)

In this method, instead of a standard protein database, a database (a SwePep database) storing amino acid sequences of known bioactive peptides is created. A peak mass-to-charge ratio detected in a mass spectrum obtained by measuring a target peptide and a mass-to-charge ratio of a theoretical fragment of the amino acid sequence in the SwePep database are collated to determine a candidate peptide.

(2) IggyPep Method (see Non Patent Literature 2)

In this method, instead of the standard protein database, a database (an IggyPep database) of amino acid sequences of proteins created by translating genomes is created. A peak mass-to-charge ratio detected in a mass spectrum obtained by measuring a target peptide and a mass-to-charge ratio of a theoretical fragment of the amino acid sequence in the IggyPep database are collated to determine a candidate peptide.

(3) HomClus Method (see Non Patent Literature 3)

In this method, an amino acid sequence candidate of a measured peptide is obtained with reference to similarity between a mass spectrum obtained by measuring a target peptide and a mass spectrum of a known peptide. A post-translational modification and a variation are estimated based on a shift amount of peaks appearing in the mass spectra.

However, even with such methods, it is not easy to accurately identify a bioactive peptide because of reasons explained below.

In the SwePep method and the IggyPep method, as in the MS/MS ion search method, only the amino acid sequence of the peptide stored in the database created in advance is a target of a search. Therefore, unless an amino acid sequence of a peptide subjected to a post-translational modification and a variation is stored in the database, it is difficult to accurately identify the peptide. In particular, in the bioactive peptide, the post-translational modification and the variation tend to occur and, moreover, a variety of the post-translational modifications and the variations occur. Therefore, peptides subjected to the post-translational modifications and the variations are often not stored in the database. As a result, the peptides are often not identified.

On the other hand, the HomClus method does not depend on the database search. Therefore, the problems of the SwePep method and the IggyPep method do not occur. However, an adequate calculation method for determining the similarity between mass spectra is not established. Therefore, it happens at high probability that correct candidate peptides are not determined when identification is actually attempted, so that the method lacks reliability of identification.

CITATION LIST

Non Patent Literature

[Non Patent Literature 1] M. Falth, et al., "Validation of Endogenous Peptide Identifications Using a Database of Tandem Mass Spectra", Journal of Proteome Research, 2008, Vol. 7, pp. 3049-3053
[Non Patent Literature 2] G. Menschaert, et al., "A Hybrid, de Novo Based, Genome-Wide Database Search Approach Applied to the Sea Urchin Neuropeptidome", Journal of Proteome Research, 2010, Vol. 9, pp. 990-996
[Non Patent Literature 3] G. Menschaert, et al., "Spectral Clustering in Peptidomics Studies Allows Homology Searching and Modification Profiling: HomClus, a Versatile Tool", Journal of Proteome Research, 2012, Vol. 11, pp. 2774-2785
[Non Patent Literature 4] M. Mann, et al., "Error-Tolerant Identification of Peptides in Sequence Databases by Peptide Sequence Tags", Analytical Chemistry, 1994, Vol. 66, pp. 4390-4399

SUMMARY OF INVENTION

Technical Problem

The present invention has been developed in view of the previously described problem, and its primary objective is to provide a mass spectrometric data analyzing apparatus and a mass spectrometric data analyzing method that can identify, with high accuracy and reliability compared with the conventional identifying method, a peptide, like a bioactive peptide, on which a cutting part of an amino acid sequence by a digestive enzyme or the like is hard to be designated.

Solution to Problem

A mass spectrometric data analyzing apparatus according to the present invention developed to solve the problems is a mass spectrometric data analyzing apparatus that identifies, based on $MS^n$ spectrum data collected by executing an $MS^n$ analysis (n is an integer equal to or larger than 2) on a test sample, a target peptide in the test sample, the mass spectrometric data analyzing apparatus including:

a) a tag database establishment section for establishing a sequence tag database in advance by obtaining, from an amino acid sequence of a known peptide and $MS^n$ spectrum information, a sequence tag, which is a partial amino acid sequence, and spectrum peak information corresponding to the sequence tag;

b) a sequence tag acquisition section for acquiring a sequence tag of the target peptide by collating peak information extracted from a measured $MS^n$ spectrum obtained for the test sample with information in the sequence tag database; and c) a peptide identification section for identifying a peptide by performing a database search in the sequence tag database or in a protein database using, as search conditions, the sequence tag for the target peptide obtained by the sequence tag acquisition section and the mass of a precursor ion deriving from the target peptide.

A mass spectrometric data analyzing method according to the present invention developed to solve the problems is a mass spectrometric data analyzing method for identifying, based on $MS^n$ spectrum data collected by executing an $MS^n$ analysis (n is an integer equal to or larger than 2) on a test sample, a target peptide in the test sample, the mass spectrometric data analyzing method including:

a) a tag database establishment step for establishing a sequence tag database in advance by obtaining, from an amino acid sequence of a known peptide and $MS^n$ spectrum information, a sequence tag, which is a partial amino acid sequence, and spectrum peak information corresponding to the sequence tag;

b) a sequence tag acquisition step for acquiring a sequence tag of the target peptide by collating peak information extracted from a measured $MS^n$ spectrum obtained for the test sample with information in the sequence tag database; and c) a peptide identification step for identifying a peptide by performing a database search in the sequence tag database or in a protein database using, as search conditions, the sequence tag for the target peptide obtained in the sequence tag acquisition step and the mass of a precursor ion deriving from the target peptide.

In the mass spectrometric data analyzing apparatus according to the present invention that carries out the mass spectrometric data analyzing method according to the present invention, the peptide identification section uses a sequence tag search method in order to identify a peptide based on information obtained from the $MS^n$ spectrum measured for the test sample. As a tool for executing the sequence tag search, for example, "Mascot Sequence Query" provided by the British manufacturer Matrix Science Ltd. is well known (see Non Patent Literature 4).

The sequence tag includes, in general, as information, a mass-to-charge ratio of a precursor ion in an $MS^n$ analysis, the mass of a certain ion P1 in an $MS^n$ spectrum, the mass of another ion P2 in a $MS^2$ spectrum, and a partial amino acid sequence corresponding to a difference between the mass of the ion P1 and the mass of the ion P2. That is, in the sequence tag search, a peptide is identified using the mass-to-charge ratio of the precursor ion, the partial amino acid sequence and a mass-to-charge ratio of a start point peak and an end point peak of the partial amino acid sequence. Compared with the MS/MS ion search, the sequence tag search method has a characteristic that it is possible to identify a peptide at high reliability even from a small number of peaks. However, it is necessary to give a sequence tag having high reliability to attain high identification accuracy.

An interval of peaks appearing in the $MS^2$ spectrum obtained by measuring the target peptide is equivalent to the molecule mass of one or a plurality of amino residues. Therefore, in general, a sequence tag is derived from an interval of peaks by de novo sequencing or the like. On the other hand, in the mass spectrometric data analyzing apparatus according to the present invention, the tag database establishment section establishes a sequence tag database (which is simply referred to as "tag database" hereinafter) in advance from information concerning a large number of peptides, amino acid sequences and the like of which are known. It is sufficient in the tag database to store only, for example, as explained above, the partial amino acid sequence, the mass-to-charge ratio of the precursor ion, the mass-to-charge ratio of the start point peak of the partial amino acid sequence, the mass-to-charge ratio of the end point peak, and the original peptide from which the partial amino acid sequence is extracted, in association with one another. An amino acid sequence length of the sequence tag can be determined appropriately. However, it is likely that, if the amino acid sequence is too short, the number of candidates is too large when a search is performed and, on the other hand, if the amino acid sequence is too long, no corresponding candidate is present when a search is performed. Therefore, it is desirable to set the amino acid sequence length to about 3 to 5.

It is preferable that, when it is known that an amino acid sequence of a sequence tag to be stored in the tag database is subjected to a post-translational modification or a variation, the tag database establishment section records information indicating to that effect in association with the sequence tag. Consequently, at a stage of sequence tag extraction by the sequence tag acquisition section, which will be described later, it is possible to also extract the sequence tag subjected to the post-translational modification or the variation. It is easier to identify a peptide subjected to the post-translational modification or the variation.

When measured $MS^n$ spectrum data obtained for the test sample is given, the sequence tag acquisition section collates peak information and the like obtained from the measured $MS^n$ spectrum with information in the tag database and acquires a sequence tag corresponding to the target peptide. In this case, coincidence of peak mass is evaluated targeting, rather than the entire amino acid sequence of the peptide, only a part of the sequence. Therefore, peptides different in portions other than the sequence are also hit. Generally, a plurality of sequence tags are extracted. Therefore, sequence tags not deriving from a right peptide are also extracted. However, sequence tags not deriving from the right peptide subjected to the post-translational modification or the variation in portions other than the sequence tags are also extracted substantially without omission. That is, although it is highly likely that a false sequence tag is included, it is less likely that a right sequence tag is omitted. In that regard, reliability of the extracted sequence tags is considered to be high.

The peptide identification section identifies, based on the sequence tag obtained by the sequence tag acquisition section, a peptide using the sequence tag search method. In that case, the peptide identification section may use the tag database created by the tag database establishment section or may use a general protein database. However, not all peptides subjected to the post-translational modification or the variation are stored in the databases. Therefore, when it is highly likely that a peptide is subjected to the post-translational modification or the variation, it is desirable to perform a database search with a condition that the peptide is subjected to the post-translational modification or the variation.

Therefore, it is desirable that, when there is a difference between the mass of a precursor ion deriving from the target peptide and the mass of a precursor ion stored in the tag database, the peptide identification section performs a database search with an additional condition that a peptide is subjected to a post-translational modification or a variation equivalent to the difference.

As explained above, in the tag database, the mass-to-charge ratio of the start point peak and the end point peak of the partial amino acid sequence is stored for each of sequence tags. It is possible to distinguish, by comparing the mass-to-charge ratio with a mass-to-charge ratio of peaks obtained from the measured $MS^n$ spectrum, whether the mass difference of the precursor ions is due to a difference in amino acid sequence of the sequence tag or a difference in an amino acid sequence other than the sequence tag. Therefore, it is desirable that, when there is a difference between the mass of a precursor ion deriving from the target peptide and the mass of a precursor ion stored in the tag database, the peptide identification section distinguishes whether the difference is present in an amino acid sequence portion corresponding to the sequence tag and, when the mass difference is present in the amino acid sequence portion corresponding to the sequence tag, performs the database search after correcting the amino acid sequence of the sequence tag to be subjected to a post-translational modification or a variation equivalent to the difference.

Consequently, even when the target peptide subjected to the post-translational modification or the variation is not stored in the database used for the sequence tag search and irrespective of in which part of an amino acid sequence total length of the peptide the amino acid sequence subjected to the post-translational modification or the variation is present, it is possible to improve the likelihood that a right target peptide can be correctly identified.

Advantageous Effects of Invention

With the mass spectrometric data analyzing apparatus and analyzing method according to the present invention, even when the target peptide subjected to the post-translational modification or the variation is not stored in the database used in identifying the peptide, it is possible to identify the target peptide with high accuracy. Further, with the mass spectrometric data analyzing apparatus and analyzing method according to the present invention, it is possible to calculate a sequence tag with high reliability for the target peptide and serve the sequence tag to the sequence tag search. Therefore, it is possible to identify the peptide with high accuracy irrespective of whether the peptide is subjected to the post-translational modification or the variation.

BRIEF DESCRIPTION OF THE DRAWINGS

FIG. 4 is a diagram showing an example of information included in a tag database.

FIG. 7 is a diagram showing a display example displayed on a screen of a display section as a result of processing in step S5 in FIG. 2.

DESCRIPTION OF EMBODIMENTS

Figure 1:
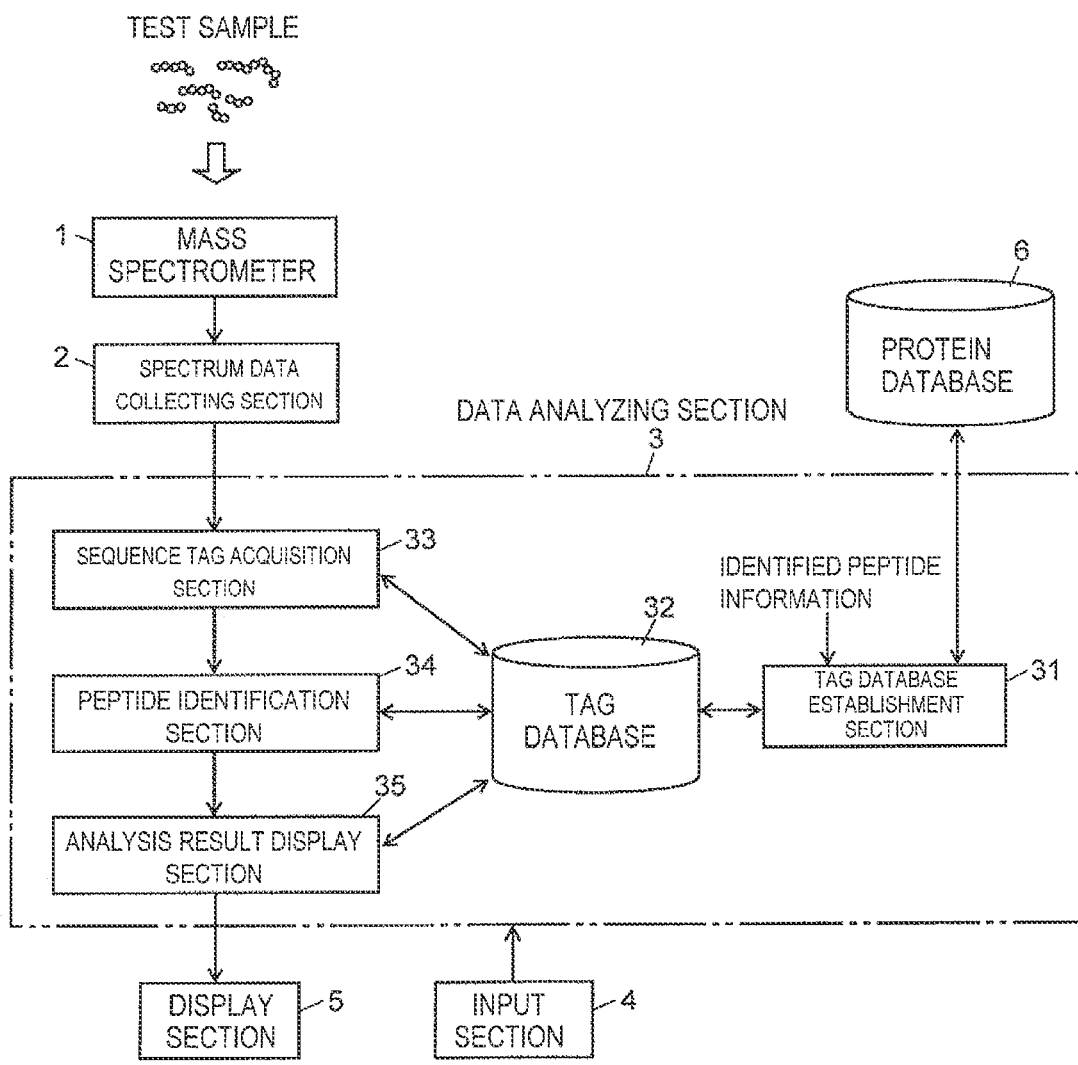
FIG. 1 is an overall configuration diagram of an embodiment of a protein identification system including a mass spectrometric data analyzing apparatus according to the present invention.

An embodiment of a protein identification system including a mass spectrometric data analyzing apparatus according to the present invention is explained below with reference to the accompanying drawings. FIG. 1 is an overall configuration diagram of the protein identification system in this embodiment.

The protein identification system according to this embodiment includes a mass spectrometer 1, a spectrum data collecting section 2, a data analyzing section 3, an input section 4, a display section 5, and a protein database 6. The data analyzing section 3 is an element equivalent to the mass spectrometric data analyzing apparatus according to the present invention. The data analyzing section 3 includes functional blocks such as a tag database establishment section 31, a tag database 32, a sequence tag acquisition section 33, a peptide identification section 34, and an analysis result display section 35. It should be noted that the protein database 6 not included in the data analyzing section 3 in FIG. 1, may be included in the data analyzing section 3. As the protein database 6, various databases (e.g., a Swiss-Prot database) generally open to the public can be used.

The elements other than the mass spectrometer 1 can be configured using a computer. Main functions can be realized by executing, on the computer, dedicated control and processing software installed in the computer.

The configuration of the mass spectrometer 1 does not matter. However, high mass accuracy and mass resolution are required. For example, an ion trap/time-of-flight mass spectrometer or a TOF/TOF mass spectrometer including an electrospray ionization (ESI) ion source or a MALDI ion source is used. In-source decay may be used instead of dissociation operation due to collision induced dissociation or the like.

Figure 2:
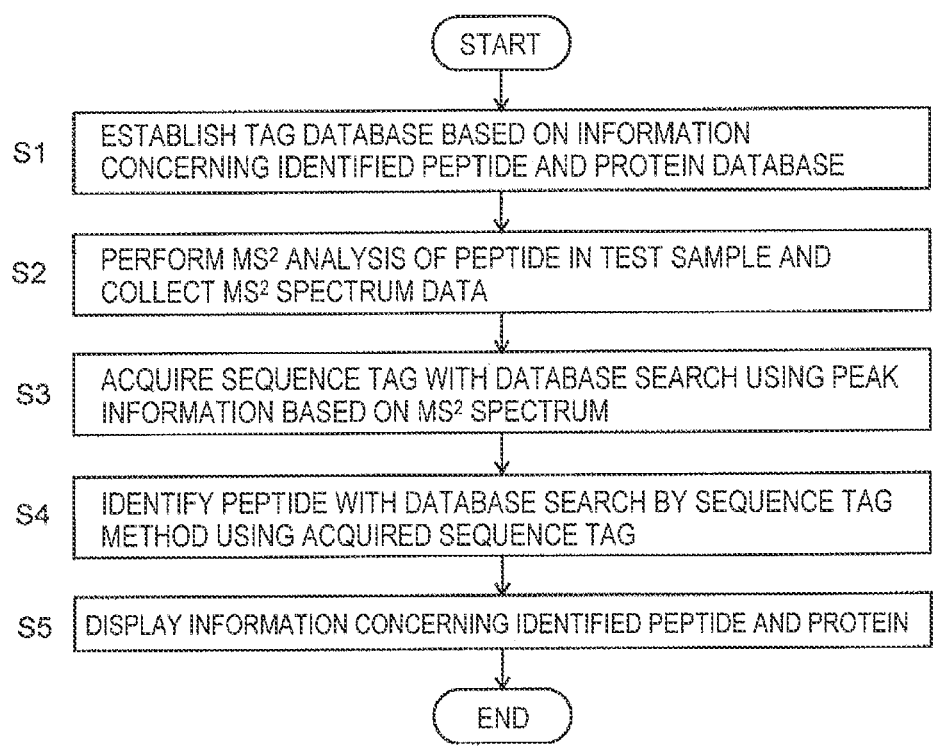
FIG. 2 is a flowchart showing a flow of schematic protein identification processing in the protein identification system in the embodiment.

FIG. 2 is a flowchart showing a flow of schematic protein identification processing in this system.

In this protein identification system, the tag database establishment section 31 establishes, based on an amino acid sequence of an identified peptide, measured $MS^n$ spectrum information and information stored in the protein database 6, the tag database 32 beforehand, that is, before execution of identification of an unknown peptide in a target test sample (step S1).

Under a situation in which the tag database 32 is established, the test sample including the unknown peptide is measured by the mass spectrometer 1. The spectrum data collecting section 2 collects and stores mass spectrum data and $MS^n$ spectrum data obtained by the mass spectrometer 1 (step S2). Typically, the spectrum data collecting section 2 only has to collect $MS^2$ spectrum data (i.e., n is 2). However, depending on a case, $MS^n$ spectrum data (n is 3 or more) is necessary.

The sequence tag acquisition section 33 reads the measured $MS^n$ spectrum data, performs a database search using the tag database 32 concerning peak information extracted from the spectrum, and obtains a sequence tag corresponding to measured data, that is, corresponding to a target peptide, which is an identification target (step S3). Generally, a plurality of sequence tags are obtained.

The obtained sequence tag is passed to the peptide identification section 34. The peptide identification section 34 performs a database search by sequence tag search using information concerning the sequence tag and information such as the mass of a precursor ion during $MS^n$ analysis execution, and identifies the target peptide (step S4). The analysis result display section 35 acquires protein information referring to the tag database 32 concerning the peptide identified in the peptide identification section 34 and displays the peptide and protein information on the display section 5 as an analysis result (step S5).

Figure 3:
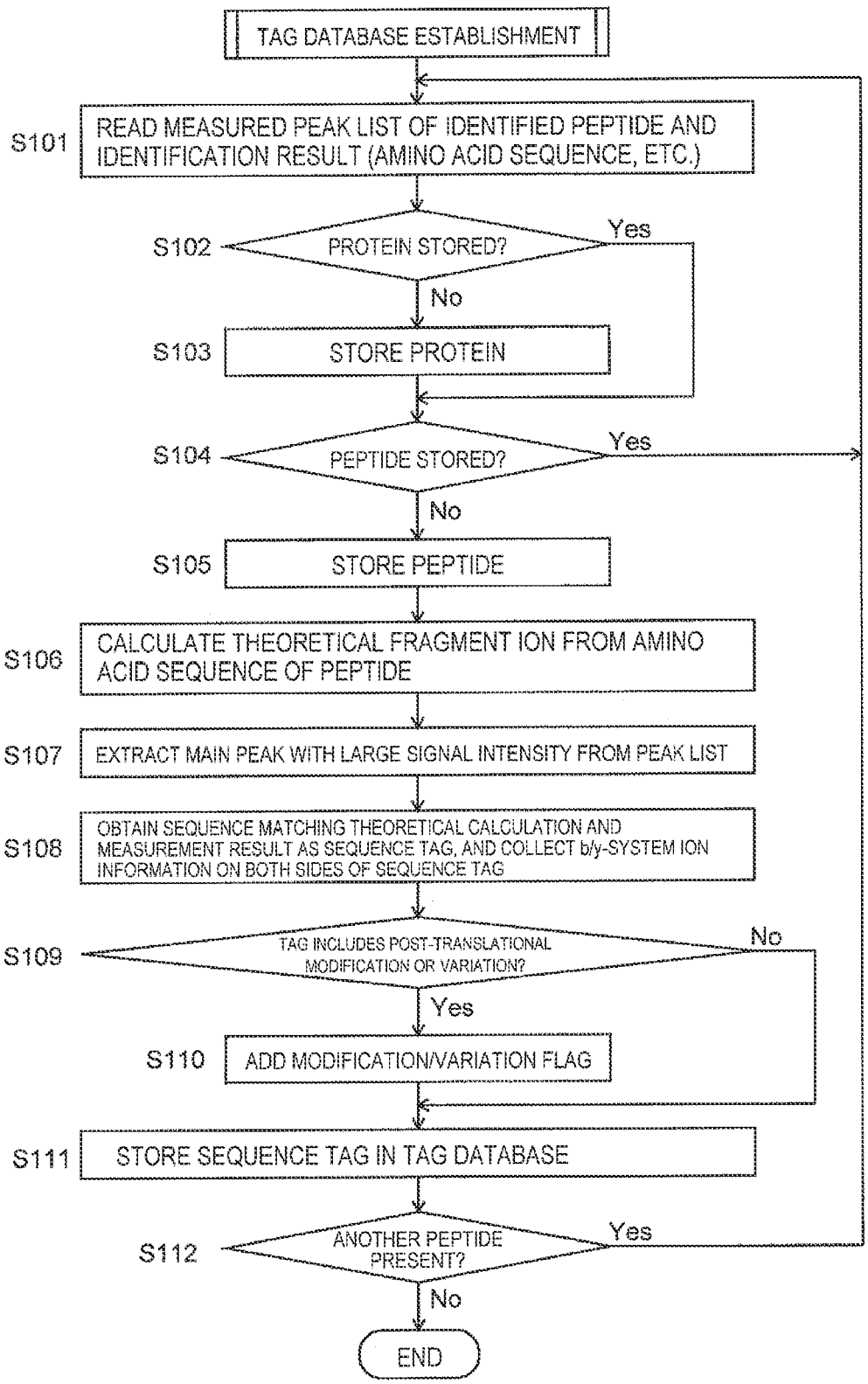
FIG. 3 is a detailed flowchart of processing in step S1 in FIG. 2.

The steps in FIG. 2 are explained in detail. FIG. 3 is a detailed flowchart of the processing in step S1 mainly carried out by the tag database establishment section 31.

First, the tag database establishment section 31 reads a peak list including information (a mass-to-charge ratio, signal intensity, etc.) concerning peaks (fragment peaks) detected in a measured $MS^n$ spectrum of already-identified one peptide and an identified amino acid sequence of the peptide together with information concerning the peptide and a protein including the peptide (step S101). Subsequently, the tag database establishment section 31 checks whether the protein including the peptide read anew is a protein already stored in the tag database 32 (step S102). When the protein is unstored, the tag database establishment section 31 sets the protein as a storing target (step S103) and checks whether the read peptide is a peptide stored in the tag database 32 (step S104). When the peptide is unstored, the tag database establishment section 31 sets the peptide as a storing target (step S105) and proceeds to step S106 and subsequent steps. When the tag database establishment section 31 determines in step S104 that the peptide is an already-stored peptide, the tag database establishment section 31 returns from step S104 to S101 and carries out the same processing concerning another identified peptide.

On the other hand, when determining that the peptide is a peptide unstored in the tag database 32, the tag database establishment section 31 calculates a mass-to-charge ratio of a theoretical fragment ion from an amino acid sequence of the peptide (step S106). The tag database establishment section 31 extracts main peaks in the peak list based on the measurement. Typically, the tag database establishment section 31 only has to extract a predetermined number of peaks in descending order of signal intensity and calculate a mass-to-charge ratio and signal intensity of the peaks (step S107). The tag database establishment section 31 obtains, based on the amino acid sequence of the peptide, the mass-to-charge ratio information of theoretical fragment ion, and the peak information based on the measurement, a partial amino acid sequence of a predetermined sequence length (a predetermined number of amino acid residues) observed in the measurement, sets the partial amino acid sequence as a sequence tag, and collects information such as a mass-to-charge ratio of a b-system ion and a mass-to-charge ratio of a y-system ion corresponding to the sequence tag (step S108).

Subsequently, the tag database establishment section 31 determines whether the obtained sequence tag is an amino acid sequence including a post-translational modification or a variation (step S109). When the sequence tag is a sequence tag including the post-translational modification or the variation, the tag database establishment section 31 adds a flag indicating to that effect (step S110). The tag database establishment section 31 stores, in the tag database 32, the amino acid sequence of the obtained sequence tag and information such as the amino acid sequence of the peptide, from which the sequence tag is obtained, the mass of the precursor ion, and the protein including the peptide. In this case, when the flag indicating that the sequence tag is the sequence tag including the post-translational modification or the variation is added, the tag database establishment section 31 also stores information concerning the flag (step S111). Thereafter, if there is another identified peptide, the tag database establishment section 31 returns from step S112 to S101 and repeats the above processing. If there is no other peptide, the tag database establishment section 31 ends the processing.

FIG. 4 is a diagram showing an example of information stored in the tag database 32. In this example, an amino acid sequence length of a sequence tag is limited to three amino acid residues. Information concerning one sequence tag includes a tag name represented by three characters of an amino acid residue ("Tag" in FIG. 4), a mass-to-charge ratio and peak intensity of a b-system fragment ion ("MassIonB" in FIG. 4), a mass-to-charge ratio and peak intensity of a y-system fragment ion ("MassIonY" in FIG. 4), a mass-to-charge ratio of a peak of maximum intensity related to "Tag" ("PilotPeak1" in FIG. 4), a mass-to-charge ratio of a peak of second largest intensity related to "Tag" ("PilotPeak2" in FIG. 4), presence/absence information concerning a post-translational modification and a variation ("Modification Tag" in FIG. 4), an identification number of a protein ("ProteinID" in FIG. 4), and an identification number of a peptide ("PeptideID" in FIG. 4).

It is found from FIG. 4 that a plurality of sequence tags are generated from the same peptide (i.e., a peptide with the same "PeptideID") included in the same protein (i.e., a protein with the same "ProteinID"). For example, in FIG. 4, all six kinds of sequence tags, "Tag" of which is DPH, PHA, HAC, ACY, CYS, and YST are sequence tags included in a protein with ProteinID=1 and generated from a peptide with PeptideID=6. Among the sequence tags, three kinds of sequence tags, "Tag" of which is HAC, ACY, and CYS, are sequence tags subjected to a post-translational modification or a variation.

The information included in the tag database 32 as explained above is created based on an actually identified peptide. Therefore, the information has high reliability. Naturally, since an amino acid sequence of the sequence tag is short, the sequence tag and the peptide are not in a one-to-one relation. As illustrated in FIG. 4, a plurality of sequence tags are associated with one peptide. Conversely, sequence tags with the same "Tag" are associated with a plurality of different peptides.

Figure 5:
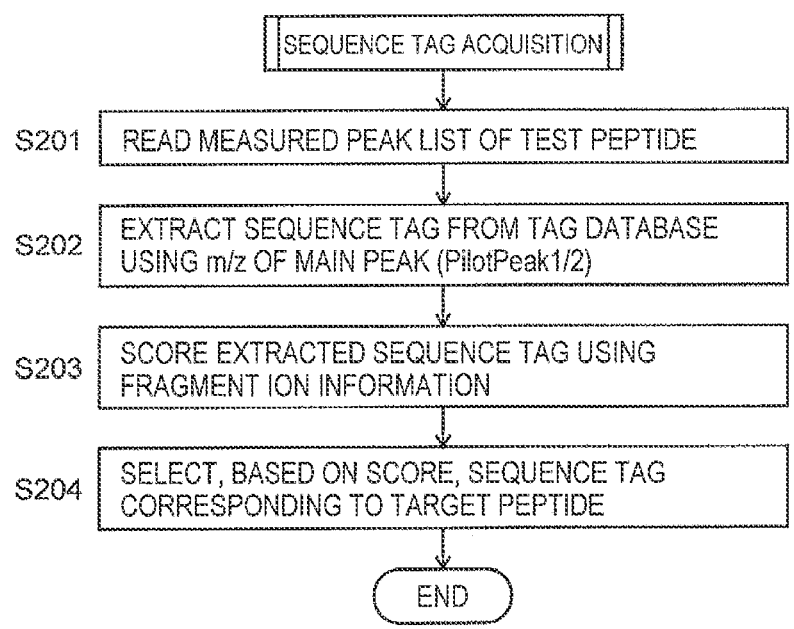
FIG. 5 is a detailed flowchart of processing in step S3 in FIG. 2.

FIG. 5 is a detailed flowchart of the processing in step S3 mainly carried out by the sequence tag acquisition section 33.

First, the sequence tag acquisition section 33 reads a peak list including information (a mass-to-charge ratio, signal intensity, etc.) of peaks detected in an MS" spectrum measured for a target peptide, an amino acid sequence of which is unknown (step S201). Subsequently, the sequence tag acquisition section 33 calculates mass-to-charge ratios of two peaks, i.e. a peak with maximum signal intensity and a peak with second largest signal intensity in the read peak list, and search and extracts from the tag database 32 a sequence tag whose "PilotPeak1" and "PilotPeak2" values are equal to (or, actually, within a predetermined allowable range from) these mass-to-charge ratios (step S202).

Further, the sequence tag acquisition section 33 scores, for a plurality of sequence tags extracted from the tag database 32, each of the sequence tags according to a signal intensity value of a peak which is included in a measured peak list and whose mass-to-charge ratios coincide with the "MassIonB" and the "MassIonY" stored in the tag database 32 (step S203). Finally, the sequence tag acquisition section 33 selects, as a sequence tag corresponding to the target peptide, a sequence tag having a high score among the sequence tags extracted earlier (step S204). In general, if one sequence tag significantly has a score higher than scores of the other sequence tags, the sequence tag acquisition section 33 only has to select the one sequence tag as the sequence tag corresponding to the target peptide. However, if the plurality of sequence tags have close scores and there is no significant difference among the scores, it is desirable to select the plurality of sequence tags as sequence tags corresponding to the target peptide.

Figure 6:
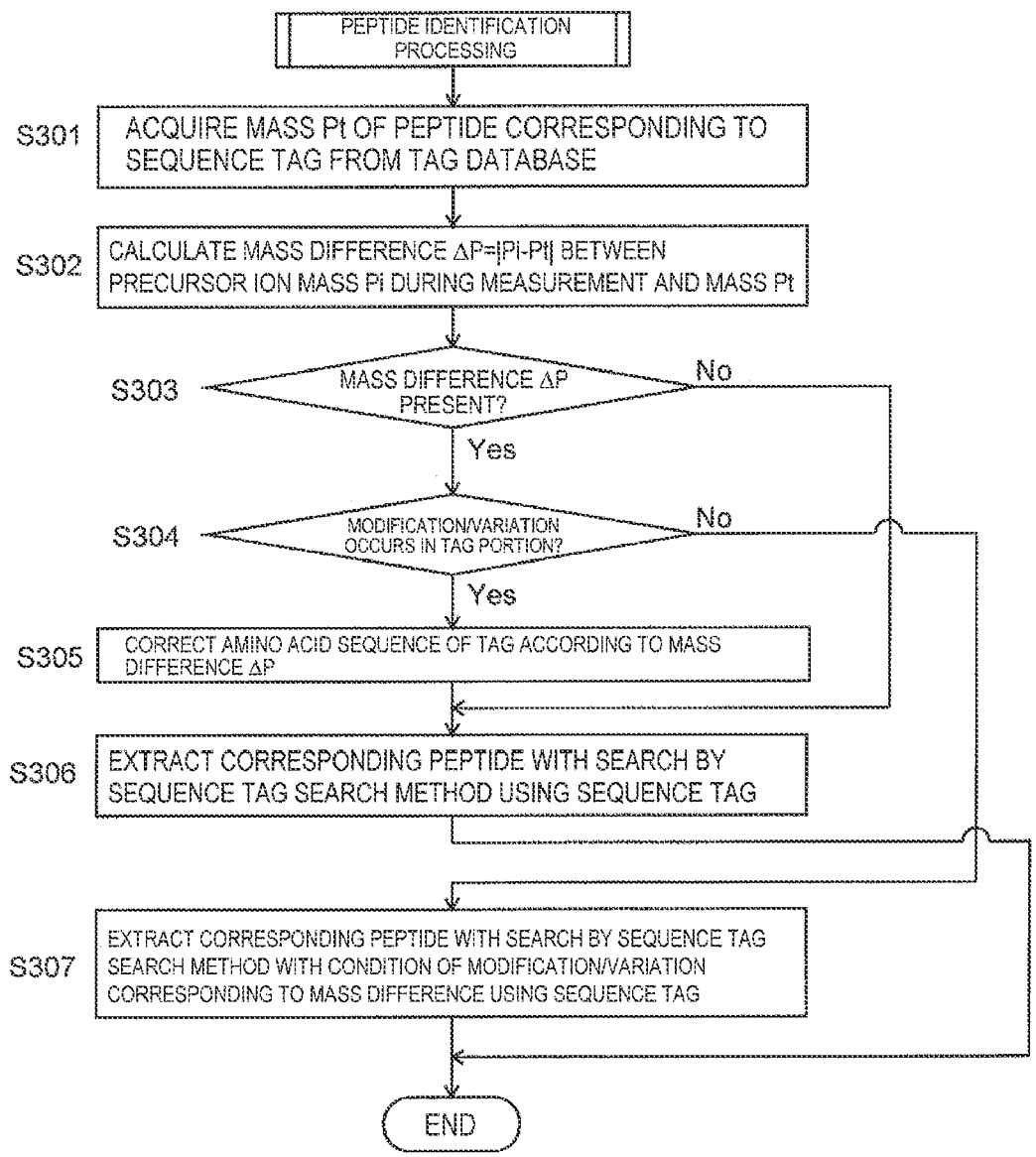
FIG. 6 is a detailed flowchart of processing in step S4 in FIG. 2.

FIG. 6 is a detailed flowchart of the processing in step S4 mainly carried out by the peptide identification section 34.

The peptide identification section 34 acquires, from the tag database 32, mass Pt of a peptide stored in the tag database 32 in association with the one or the plurality of sequence tags determined in step S3 (step S301). The peptide identification section 34 determines whether there is a difference between the mass Pt of the peptide and mass Pi of a precursor ion obtained by an $MS^2$ analysis of the target peptide. That is, the peptide identification section 34 calculates a mass difference $\Delta P=|Pi-Pt|$ (S302) and determines whether there is a mass difference by determining whether $\Delta P$ is equal to or smaller than a predetermined allowable value (step S303).

When it is determined in step S303 that there is no mass difference, it is possible to determine that the determined sequence tag is appropriate. Therefore, the peptide identification section 34 searches for, in the tag database 32, a peptide including the sequence tag selected in step S3, that is, the partial amino acid sequence indicated by "Tag" and having an amino acid sequence whose mass-to-charge ratio of the precursor ion and a mass-charge ratio in a C terminus direction and a mass-to-charge ratio in an N terminal direction from the partial amino acid sequence indicated by "Tag" coincide with those of the selected sequence tag (step S306).

Specifically, the peptide identification section 34 only has to execute a sequence tag search such as "Mascot Sequence Query". When the "Mascot Sequence Query" is used, a score and an expected value indicating reliability of the database search to the peptide hit by the database search are added. Therefore, even when a plurality of peptides are hit, if a reliability index value of certain one peptide is significantly higher than reliability index values of the other peptide, only the peptide has to be listed as an identified peptide. When only one peptide cannot be identified, for example, when there is no significant difference among the reliability index values, a plurality of likely peptides have to be selected as candidates together with the reliability index values.

When it is determined in step S303 that there is the mass difference $\Delta P$, it is likely that this mass difference occurs due to a post-translational modification or a variation. Therefore, the peptide identification section 34 determines whether a post-translational modification or a variation occurs in a portion of the sequence tag by determining whether there is the same mass difference $\Delta P$ in mass-to-charge ratios of fragment ions of the b system and the y system (step S304). When it is determined that there is the same mass difference in the mass-to-charge ratios of the fragment ions, it is possible to determine that a post-translational modification or a variation occurs in the sequence tag. Therefore, the peptide identification section 34 corrects the amino acid sequence of the sequence tag estimating a post-translational modification or a variation according to the mass difference (step S305) and then proceeds to step S306. When it is determined that there is no mass difference in the mass-to-charge ratio of the fragment ions, that is, it is determined that a post-translational modification or a variation does not occur in the sequence tag (No in step S304), the peptide identification section 34 searchers for a corresponding peptide through a database search using the sequence tag search method or the like under a condition that a known post-translational modification or variation estimated from the mass difference occurs (step S307).

As explained above, in data analysis processing in the protein identification system in this embodiment, even when a post-translational modification or a variation occurs in the peptide, it is possible to perform the peptide search using the database search after estimating, to a certain degree, a portion subjected to the modification or the variation. Therefore, it is possible to expect identification at high accuracy.

Figure 7:
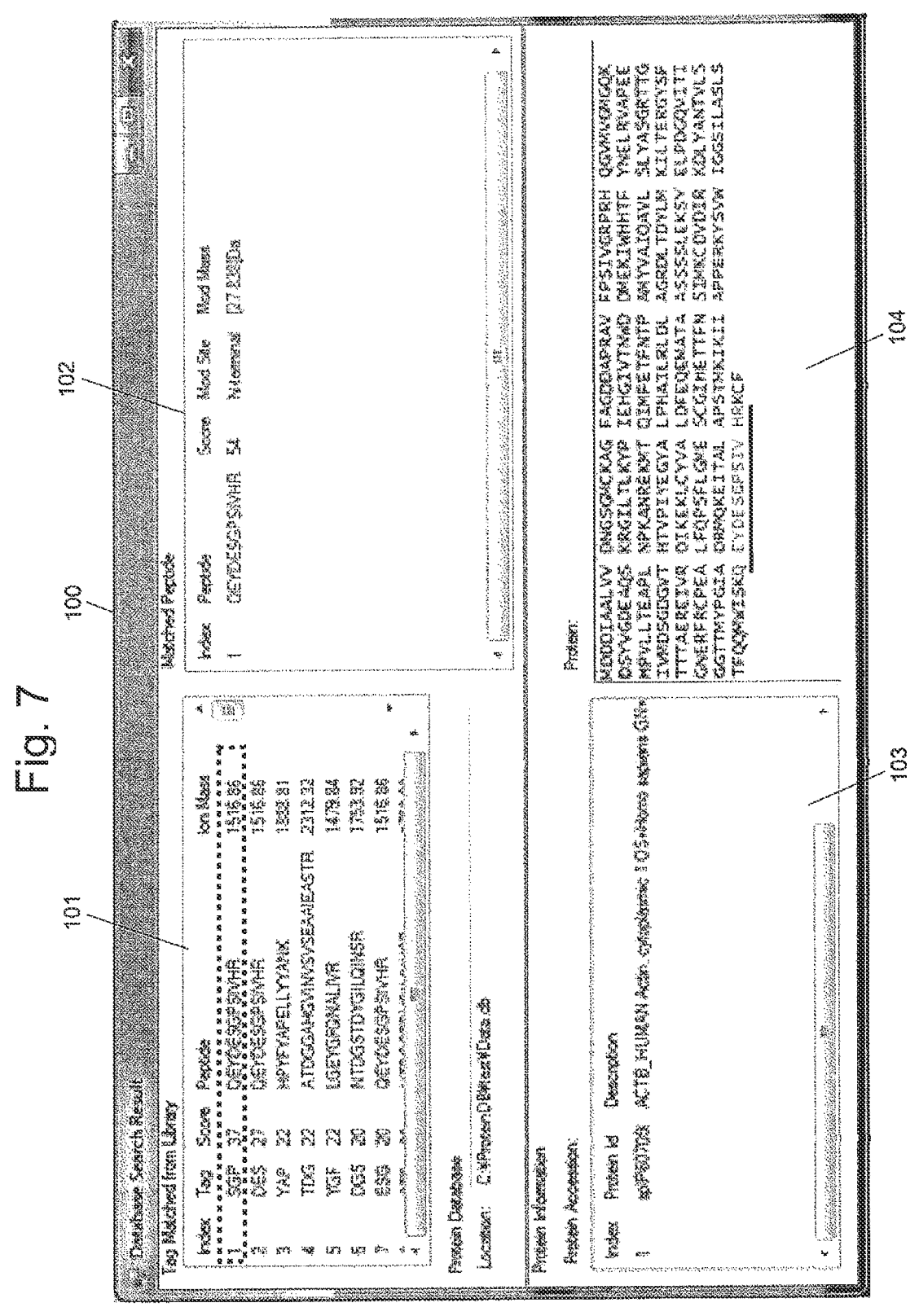
Figure 8:
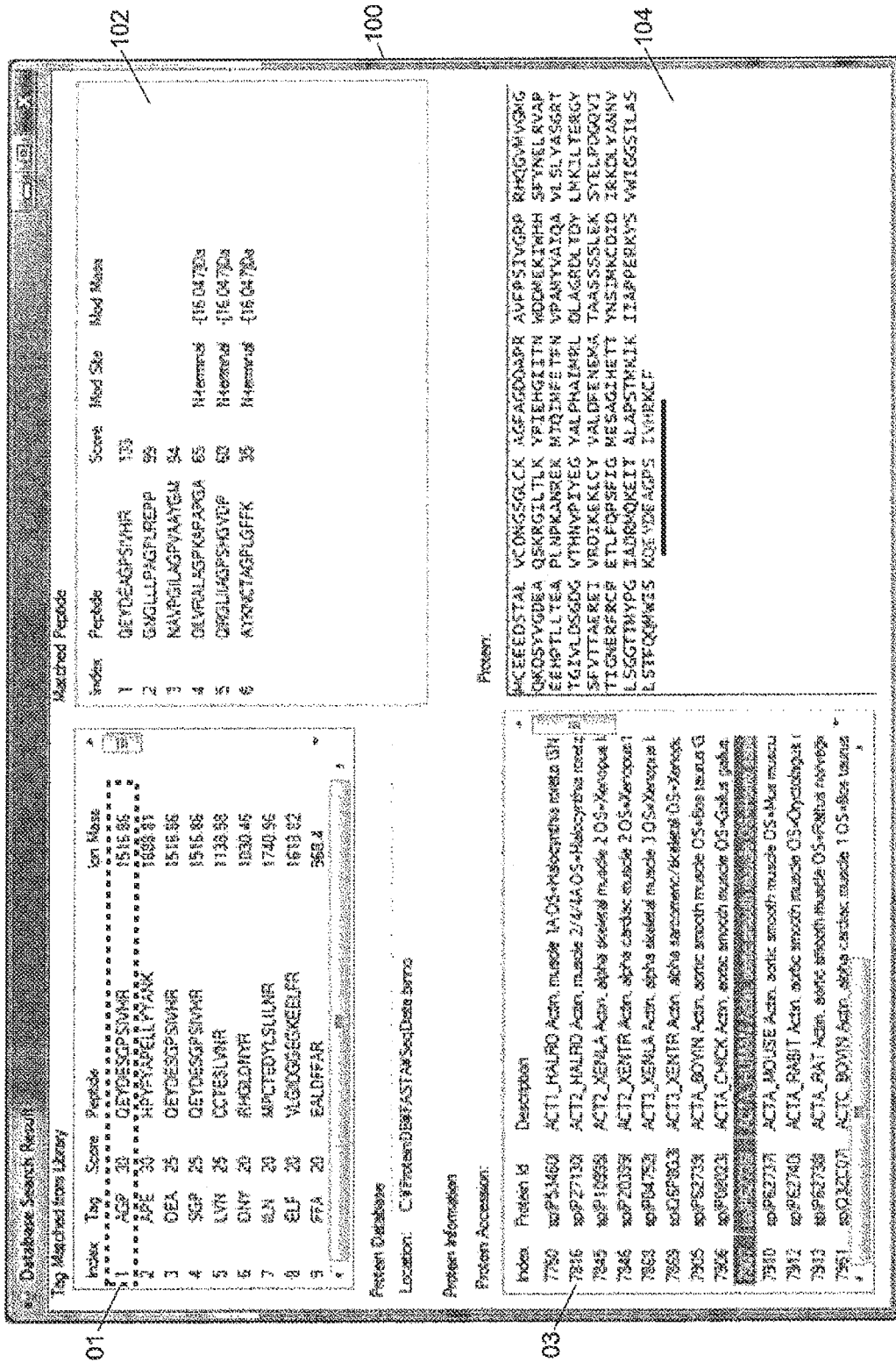
FIG. 8 is a diagram showing another display example displayed on the screen of the display section as a result of the processing in step S5 in FIG. 2.

FIGS. 7 and 8 are respectively display examples displayed on the screen of the display section 5 as a result of the processing in step S4.

On a result display screen 100, sequence tags obtained as a result of the search in step S3 are displayed as a list in a tag search result display field 101 in an upper left part. An amino acid sequence of a peptide obtained by the search in step S4 is displayed as a list in a peptide search result display field 102 in an upper right part. As reference information, a protein information display field 103 indicating a protein including the peptide is arranged in a lower left part. A protein and amino acid sequence display field 104 indicating an amino acid sequence of the entire protein displayed or selected in the protein information display field 103 is arranged in a lower right part.

In the example shown in FIG. 7, a mass-to-charge ratio of the precursor ion in the $MS^2$ analysis for the target peptide is 1544 Da.

The tag search result display field 101 in FIG. 7 indicates that an amino acid sequence of a sequence tag hit in a first rank is SGP, a score indicating reliability of the search is 37, and the sequence tag is stored in the tag database 32 based on a measurement result and an identification result of a peptide, an amino acid sequence of which is QEYDESGPSIVHR (having the mass of 1516.86). The peptide search result display field 102 indicates that an amino acid sequence subjected to a post-translational modification or a variation (in this example, subjected to a post-translational modification called Formyl (N-term)) of 27.838 Da to an N terminus side from a portion equivalent to the sequence tag with respect to the peptide, the amino acid sequence of which is QEYDESGPSIVHR is hit.

In the protein and amino acid sequence display field 104, a peptide portion hit by the search in the amino acid sequence of the protein is displayed in color with red characters (In FIG. 7, an underline is added instead of the color display). Consequently, it is possible to immediately understand to which portion in the total length of protein the identified peptide corresponds.

In the example shown in FIG. 8, a mass-to-charge ratio of the precursor ion in the $MS^2$ analysis for the target peptide is 1502 Da.

In this example, a sequence tag, an amino acid sequence of which is AGP, is hit in the first place. This is a variation of the amino acid sequence SGP stored in the tag database 32. A mass-to-charge ratio of the measured precursor ion is 1502 Da. This is larger by the mass of one proton (about 1 Da). Therefore, in the database search by the sequence tag search method, the database search is performed under a condition that the amino acid sequence is subjected to a post-translational modification or a variation of −16.16 Da (=1500.7−1516.86). A peptide in which an amino acid residue S sixth from an N terminus of the amino acid sequence of QEYDESGPSIVHR is varied to A is identified.

In the protein and amino acid sequence display field 104, as in FIG. 7, a peptide portion hit by the search in the amino acid sequence of the protein is displayed in color with red characters.

In this way, in the protein identification system in this embodiment, even a peptide subjected to a post-translational modification or a variation is accurately identified. An amino acid sequence of the peptide, information concerning a protein including the peptide, a position of an identified amino acid sequence in the amino acid sequence of the protein, and the like are clearly presented to an analyst by the result display screen 100.

It is preferable that information concerning the peptide identified in this way is stored in the tag database 32 according to the flowchart shown in FIG. 3. Consequently, the tag database 32 itself is enriched every time a new peptide is identified. Improvement of accuracy of identification can be expected.

In the embodiment, after the sequence tag corresponding to the target peptide is obtained, the database search by the sequence tag search method using the sequence tag is executed on the tag database 32. Alternatively, the database search by the sequence tag search method using the sequence tag may be applied to the general protein database 6. Only the information based on the identified peptide is stored in the tag database 32, while a wide range of information is stored in the protein database 6. Therefore, a wide range of proteins can be set as search targets. Consequently, for example, it is possible to identify a protein of a rat, that has high homology with a mouse, using a protein database of a mouse.

It should be noted that the previous embodiment is a mere example of the present invention, and any change, modification or addition appropriately made within the spirit of the present invention will naturally fall within the scope of claims of this patent application.

REFERENCE SINGS LIST

1 . . . Mass Spectrometer
2 . . . Spectrum Data Collecting Section
3 . . . Data Analyzing Section
4 . . . Input Section
5 . . . Display Section
6 . . . Protein Database
31 . . . Tag Database Establishment Section
32 . . . Tag Database
33 . . . Sequence Tag Acquisition Section
34 . . . Peptide Identification section
35 . . . Analysis Result Display Section
100 . . . Result Display Screen
101 . . . Tag Search Result Display Field
102 . . . Peptide Search Result Display Field
103 . . . Protein Information Display Field
104 . . . Protein and Amino Acid Sequence Display Field

The invention claimed is:

1. A mass spectrometric apparatus that identifies a target peptide in a test sample based on $MS^n$ spectrum data, comprising:
 a mass spectrometer that performs an $MS^n$ analysis (n is an integer equal to or larger than 2) on the test sample to provide the $MS^n$ spectrum data, which indicates dissociated ions of the test sample; and
 a data analyzing section including a sequence tag database and configured for:
  a) establishing the sequence tag database in advance obtaining, from an amino acid sequence of a known peptide and $MS^n$ spectrum information, a sequence tag, which is a partial amino acid sequence, and spectrum peak information corresponding to the sequence tag;
  b) acquiring a sequence tag of the target peptide by collating peak information extracted from a measured $MS^n$ spectrum obtained for the test sample with information in the sequence tag database; and c) identifying a peptide by performing a database search in the sequence tag database or in a protein database using, as search conditions, the sequence tag for the target peptide obtained by the acquiring the sequence tag and mass of a precursor ion deriving from the target peptide.

2. The mass spectrometric apparatus according to claim 1, wherein the establishing the sequence tag database includes storing information indicating that an amino acid sequence of a sequence tag is subjected to a post-translational modification or a variation in association with the sequence tag when an amino acid sequence of a sequence tag is subjected to a post-translational modification or variation.

3. The mass spectrometric apparatus according to claim 1, wherein the identifying the peptide includes performing a database search with an additional condition that a peptide is subjected to a post-translational modification or a variation equivalent to a difference between mass of a precursor ion deriving from the target peptide and mass of a precursor ion stored in the sequence tag database when there is a difference between mass of a precursor ion deriving from the target peptide and mass of a precursor ion stored in the sequence tag database.

4. The mass spectrometric apparatus according to claim 2, wherein the identifying the peptide includes performing a database search with an additional condition that a peptide is subjected to a post-translational modification or a variation equivalent to a difference between mass of a precursor ion deriving from the target peptide and mass of a precursor ion stored in the sequence tag database when there is a difference between mass of a precursor ion deriving from the target peptide and mass of a precursor ion stored in the sequence tag database.

5. The mass spectrometric apparatus according to claim 3, wherein
the identifying the peptide includes distinguishing, when there is a difference between mass of a precursor ion deriving from the target peptide and mass of a precursor ion stored in the tag database, whether the difference is present in an amino acid sequence portion corresponding to the sequence tag, and
performing, when the difference is present in the amino acid sequence portion corresponding to the sequence tag, the database search after correcting the amino acid sequence of the sequence tag to be subjected to a post-translational modification or a variation equivalent to the difference.

6. The mass spectrometric apparatus according to claim 4, wherein
the identifying the peptide includes distinguishing, when there is a difference between mass of a precursor ion deriving from the target peptide and mass of a precursor ion stored in the tag database, whether the difference is present in an amino acid sequence portion corresponding to the sequence tag, and
performing, when the difference is present in the amino acid sequence portion corresponding to the sequence tag, the database search after correcting the amino acid sequence of the sequence tag to be subjected to a post-translational modification or a variation equivalent to the difference.

7. A mass spectrometric method for identifying a target peptide in a test sample, comprising:
performing by a mass spectrometer an $MS^n$ analysis (n is an integer equal to or larger than 2) on the test sample to provide $MS^n$ spectrum data which indicates dissociated ions of the test sample;
a) establishing a sequence tag database in advance by obtaining, from an amino acid sequence of a known peptide and $MS^n$ spectrum information, a sequence tag, which is a partial amino acid sequence, and spectrum peak information corresponding to the sequence tag;
b) acquiring a sequence tag of the target peptide by collating peak information extracted from a measured $MS^n$ spectrum obtained for the test sample with information in the sequence tag database; and
c) identifying a peptide by performing a database search in the sequence tag database or in a protein database using, as search conditions, the sequence tag for the target peptide obtained in the sequence tag acquisition step and mass of a precursor ion deriving from the target peptide.

8. The mass spectrometric method according to claim 7, wherein, when an amino acid sequence of a sequence tag is subjected to a post-translational modification or a variation, information indicating to that effect is stored in association with the sequence tag.

9. The mass spectrometric method according to claim 7, wherein, when there is a difference between mass of a precursor ion deriving from the target peptide and mass of a precursor ion stored in the tag database, a database search is performed with an additional condition that a peptide is subjected to a post-translational modification or a variation equivalent to the difference.

10. The mass spectrometric method according to claim 8, wherein, when there is a difference between mass of a precursor ion deriving from the target peptide and mass of a precursor ion stored in the tag database, a database search is performed with an additional condition that a peptide is subjected to a post-translational modification or a variation equivalent to the difference.

11. The mass spectrometric method according to claim 9, wherein
when there is a difference between mass of a precursor ion deriving from the target peptide and mass of a precursor ion stored in the tag database, it is distinguished whether the difference is present in an amino acid sequence portion corresponding to the sequence tag, and
when the difference is present in the amino acid sequence portion corresponding to the sequence tag, the database search is performed after the amino acid sequence of the sequence tag is corrected to be subjected to a post-translational modification or a variation equivalent to the difference.

12. The mass spectrometric method according to claim 10, wherein
when there is a difference between mass of a precursor ion deriving from the target peptide and mass of a precursor ion stored in the tag database, it is distinguished whether the difference is present in an amino acid sequence portion corresponding to the sequence tag, and
when the difference is present in the amino acid sequence portion corresponding to the sequence tag, the database search is performed after the amino acid sequence of the sequence tag is corrected to be subjected to a post-translational modification or a variation equivalent to the difference.

* * * * *